United States Patent
Le Comte et al.

(10) Patent No.: US 8,623,297 B2
(45) Date of Patent: Jan. 7, 2014

(54) DEVICE FOR THE PREPARATION AND FRACTIONED DISPENSING OF FLUID SAMPLES, DISPENSING SYSTEM INCLUDING SUCH DEVICE AND RELATED METHOD

(75) Inventors: Roger Le Comte, Perols (FR); Guilhem Couderc, Saint Jean de Vedas (FR); Paul Moreno, Montpellier (FR)

(73) Assignee: Horiba ABX SAS, Montipellier (FR)

( * ) Notice: Subject to any disclaimer, the term of this patent is extended or adjusted under 35 U.S.C. 154(b) by 859 days.

(21) Appl. No.: 12/671,747

(22) PCT Filed: Jul. 29, 2008

(86) PCT No.: PCT/FR2008/051428
§ 371 (c)(1),
(2), (4) Date: Feb. 2, 2010

(87) PCT Pub. No.: WO2009/024710
PCT Pub. Date: Feb. 26, 2009

(65) Prior Publication Data
US 2011/0189713 A1    Aug. 4, 2011

(30) Foreign Application Priority Data
Aug. 3, 2007 (FR) ..................... 07 56922

(51) Int. Cl.
*B01L 3/02* (2006.01)
*B01L 99/00* (2010.01)
*G01N 35/02* (2006.01)
*G01N 35/08* (2006.01)
*G01N 35/10* (2006.01)

(52) U.S. Cl.
USPC ........... 422/512; 422/514; 422/515; 422/520; 422/546; 436/47; 436/49; 436/52; 73/864.01; 73/864.22; 600/576

(58) Field of Classification Search
USPC ............. 422/512, 514–515, 520, 546; 436/49
See application file for complete search history.

(56) References Cited

U.S. PATENT DOCUMENTS 3,719,086 A    3/1973   Bannister et al.
3,911,749 A *  10/1975  Hendry ...................... 73/864.22
(Continued)

FOREIGN PATENT DOCUMENTS

EP    0 543 544 A1    5/1993
EP    0 913 680 A1    5/1999
(Continued)

*Primary Examiner* — Jill Warden
*Assistant Examiner* — Julie Tavares
(74) *Attorney, Agent, or Firm* — Clark & Brody

(57) ABSTRACT

The present invention relates to a device, to a system, and to a method for the preparation and fractioned dispensing of samples of a fluid. The device of the invention comprises a body having formed therein guide means suitable for receiving a sample-taker member and for guiding it in translation through the device, and at least one preparation chamber enabling an aliquot of a fluid sample dispensed into the chamber by a said sample-taker member to be prepared in a stream of a suitable reagent. The guide means pass through the preparation chamber and communicate therewith to enable an aliquot of fluid to be dispensed into the chamber in a determined position of the sample-taker member in the guide means. The preparation chamber has an introduction orifice for introducing at least one reagent into the chamber for mixing the reagent with an aliquot, and at least one dispensing orifice for dispensing the mixture formed by said aliquot and said reagent to recovery and/or analysis means.

17 Claims, 5 Drawing Sheets

(56) References Cited

U.S. PATENT DOCUMENTS

| | | | |
|---|---|---|---|
| 4,888,998 A | | 12/1989 | Buzza et al. |
| 5,254,313 A | | 10/1993 | Kuroda et al. |
| 5,569,861 A | * | 10/1996 | Le Comte et al. ......... 73/864.22 |
| 5,853,665 A | | 12/1998 | Ade et al. |
| 2006/0099716 A1 | | 5/2006 | Tipler et al. |

FOREIGN PATENT DOCUMENTS

| | | |
|---|---|---|
| FR | 2 622 692 A1 | 5/1989 |
| FR | 2 767 583 A1 | 2/1999 |
| GB | 2 025 900 A | 1/1980 |
| WO | 2005/010488 A2 | 2/2005 |
| WO | 2008/012445 A1 | 1/2008 |

* cited by examiner

DEVICE FOR THE PREPARATION AND FRACTIONED DISPENSING OF FLUID SAMPLES, DISPENSING SYSTEM INCLUDING SUCH DEVICE AND RELATED METHOD

The present invention relates to the field of analyzing fluids, whether biological or otherwise.

FIELD OF THE INVENTION

The field of the invention is in particular that of analyzing biological fluids such as blood, whether of human or animal origin, and in particular the field of hematological analyses and designing systems and methods for performing such analyses in automatic manner.

More particularly, the present invention relates to a device for the preparation and fractioned dispensing of blood samples for automatic analysis, such as an automatic system for sampling, preparing, and fractioned dispensing of blood samples including such a device, and a method of preparing and dispensing of blood samples using such a system.

In the present application, the term "blood sample" is used to mean a volume of blood taken from a specimen of blood taken from a patient, mixed with an anticoagulant, and contained in a container, such as a tube that is opened or closed by a stopper, and that has not been subjected to treatment and has not suffered spoiling. Conventionally, such a blood sample is said to be total or complete.

Analyzing blood samples serves to measure various parameters and to count various component elements of the blood, thereby obtaining information about the state of health of patients.

Such parameters include, in particular, counts of red and white blood corpuscles, hemoglobin, or indeed platelets.

Such analyses are performed using automatic appliances (analyzers) that incorporate automatic systems for sampling samples and making measurements that make it possible to determine the contents of various elements of interest in patients' blood.

In order to measure the parameters of interest in a blood sample, it is necessary for said sample to be fractioned into small portions of determined volume, generally referred to as aliquots. These aliquots are prepared (in practice mixed) using various reagents making it possible to determine the values of parameters of the blood sample in the aliquots made from the initial blood sample, with this in particular being done by optical measuring systems, thereby obtaining analysis results for all of the elements of interest.

In order to optimize analysis rates, and also in order to minimize the volumes of reagents used, the various aliquots of blood needed for performing analyses are obtained from a single sample of blood taken on a single occasion and contained in a tube, the aliquots being taken by appropriate means.

BACKGROUND OF THE INVENTION

At present, various types of device are known for fractioning a blood sample into multiple aliquots and for mixing them with reagents suitable for these various different analyses that are to be performed.

Firstly, sampling valves are known, e.g. such as those taught by French patent application FR 2 622 692 in the name of the Applicant.

Such sampling valves enable automatic analyzers to operate at a high rate and they are conventionally used only in top-of-range appliances since such valves are expensive to fabricate and to adjust.

Furthermore, sampling valves present the drawback of requiring regular and complex maintenance, thus making them more expensive to operate. Also, sampling valves present the drawback of requiring volumes of blood that are greater than the volumes theoretically necessary for performing analyses.

Other systems have been developed for fractioning a sample of blood. By way of example, mention may be made of documents U.S. Pat. No. 5,254,313 or EP 0 543 544 filed in the name of TOA Medical. In both those documents, the blood sample is taken from an open tube, and there is no system for piercing a tube stopper. The blood fractions (or aliquots) are mixed with the reagent(s) in one or more mixing vessels. Finally, it is a moving portion of the valve that enables aliquoting.

Mention may also be made of patent WO 2005/010488 filed by Dade Behring, in which samples can be taken from a tube that is closed by a stopper. However in that document also, the mixing of the sample with the reagent takes place in a mixing vessel. In addition, the sample-taker needle needs to be moved horizontally over the mixing vessel.

Another type of system is also known for fractioning a blood sample into multiple aliquots, and is described in patent application EP 0 913 680 A1 in the name of the Applicant.

The device described in that document has a sample-taker member made up of a first striker tube for piercing a tube from which a sample of blood is to be taken, and for admitting air into the tube, and a needle mounted coaxially inside the striker to take the sample of blood from the tube and then dispense various aliquots from the sample taken from the tube into respective streams of reagent within different analysis vessels. The sample-taker member of the system is connected to a syringe for sucking up a determined volume of blood from the tube of blood for analysis, and then for dispensing the aliquots mixed with the appropriate reagents into the various analysis vessels. Said sample-taker member is mounted on a device that is movable in translation both vertically and horizontally by motor-driven means in order to be capable of entering into tubes of blood to take the samples of blood for analysis therefrom, and then dispense respective aliquots of blood into each of the measurement vessels. The system thus enables multiple aliquots to be dispensed from a single sample of blood in very accurate manner without the above-described drawbacks of sampling valves.

Nevertheless, the fractioned dispensing system described in EP 0 913 680 A1 is not entirely satisfactory either.

The multiple movements of the sample-taker member firstly for taking the sample of blood from the tube and subsequently for dispensing the various aliquots of said sample into the analysis vessels require the mechanical systems that move the sample-taker member to be adjusted accurately. It is also possible to observe a certain amount of variation over time in the accuracy with which the sample-taker member is positioned when dispensing blood aliquots into the analysis vessels relative to the orifices for introducing reagents into said vessels.

Furthermore, under certain very particular conditions, the sample-taker member of the system with a coaxial striker and sample-taker needle can suffer from dirtying as a result of successive piercing operations of the same tube, so that small pieces of stopper or of dried blood can become engaged between the needle and the inside body of the striker, thereby disturbing the preparation of aliquots.

OBJECT AND SUMMARY OF THE INVENTION

The object of the present invention is to provide a device for the preparation and fractioned dispensing of fluid samples, and more particularly samples of blood, that makes it possible to solve, or at least to attenuate, the problems of fractioned dispensing devices known in the prior art.

Another object of the invention is to provide a device for preparation and fractioned dispensing that is simpler and less expensive to make than previously known systems, and that is also simpler to maintain over time.

Another object of the invention is to provide a device for the fractioned dispensing of blood samples that enables work to be performed at a faster rate than the rate made possible by the dispensing system described in EP 0 913 680 A1.

Another object of the invention is also to provide a device for the preparation and fractioned dispensing of blood samples that makes it possible to eliminate the problems of the sample-taker members becoming dirtied and of blood samples being contaminated prior to analysis, and that also makes it possible to limit the volumes of reagents used for diluting and analyzing blood samples.

In order to achieve these various objects, the present invention proposes a device for the preparation and fractioned dispensing of fluid samples, in particular of blood contained in a tube, wherein the device comprises a body having formed therein:
- guide means adapted to receive a sample-taker member for taking samples of a fluid and for guiding it in translation within the device along an axis YY', the guide means being constituted by a channel passing through the device along the axis YY' and opening out in opposite sides of said device, the channel being shaped to receive the fluid sample-taker member and to guide it in translation along the axis YY' through the device until the end of the sample-taker member is introduced into the tube containing the fluid; and
- at least one preparation chamber enabling an aliquot of a sample of fluid dispensed in the chamber by said sample-taker member to be prepared in a stream of an appropriate reagent; and
- the guide means passing through the preparation chamber and communicating therewith in such a manner as to enable a said aliquot of a said fluid sample to be dispensed into the chamber by the sample-taker member in a determined position thereof within the guide means; and
- the preparation chamber including an introduction orifice for introducing at least one reagent into the chamber for mixing the reagent with a said aliquot, and at least one dispensing orifice for dispensing the mixture formed by said aliquot and said reagent to recovery and/or analysis means.

The body of the device of the invention is advantageously formed as a single piece or as a plurality of pieces of a biologically inert material such as, for example: polymethyl methacrylate (PMMA), polypropylene, polyethylene, glass, Teflon®, PEEK®, or indeed stainless steel, and having said guide means and said dilution chamber(s) machined, injected, or thermoformed therein.

The device of the invention makes it possible in particular to prepare and dispense fractions of samples of fluid such as blood, e.g. in the form of multiple aliquots with full operating safety, and without risk of dirtying or blocking, in compact manner, and while ensuring that preparation is very accurate.

Prior to being dispensed into recovery and/or analysis means, fluid aliquots are prepared directly in at least one preparation chamber that is incorporated in the device, and not in auxiliary reaction vessels. This eliminates stabilization problems associated with the various movements of the sample-taker members for dispensing aliquots in auxiliary vessels. Furthermore, the invention also makes it possible to reduce the overall size of the analyzer and to reduce the number of motors needed to operate the device. This serves to reduce risks associated with mechanical elements.

The device of the invention is also modular in that it makes it possible, where necessary, to have a plurality of preparation chambers in a stack, preferably one above another, thus enabling multiple different aliquots of a fluid sample to be prepared and dispensed almost simultaneously, merely by moving a sample-taker member through a few millimeters in the guide duct of the device.

The device also makes it possible to prepare and dispense a plurality of aliquots in the same preparation chamber in succession.

In order for the sample-taker member to pass right through the device prior to being introduced in the tube, it is necessary for the tube, i.e. the receptacle containing the fluid for analysis, to be presented to the surface of the body that is opposite from the surface through which the sample-taker member penetrates into the body of the device. Typically, the tube is presented under the device facing the orifice of the guide means in the bottom surface of the device, while the sample-taker member is introduced into the guide means of the device through the top surface thereof, and passes through the device before penetrating into the tube in order to suck up the fluid for analysis therefrom.

Thus, this preparation and dispensing device does not have any moving parts, thereby making the overall system very robust. The device of the invention serves to guide the sample-taker member, conventionally a needle, along a single axis. The sample-taker member thus no longer moves in horizontal manner as in prior art devices for fractioned dispensing when sampling the fluid and dispensing the various fluid aliquots, and thus it avoids the drawbacks of those systems.

In accordance with another preferred characteristic of the invention, the preparation chamber(s) is/are constituted by a channel passing through the device, thereby forming two orifices, respectively the introduction orifice and the dispensing orifice of the preparation chamber.

The mixing with the reagents thus takes place directly inside the device in the preparation chamber(s), and no longer in auxiliary vessels, as proposed in the prior art. This configuration makes it possible to reduce the overall size of the device, and to eliminate any risk of the prepared aliquots being dirtied.

Still according to the invention, the preparation chamber(s) is/are constituted by a said channel oriented along an axis that is preferably perpendicular to said axis YY' of said guide means.

This configuration makes it easier to dispense fluid aliquots quickly in the preparation chamber(s) and to prepare them with the reagents in said chamber(s).

In accordance with another advantageous characteristic, the device includes cleaner means for cleaning a said sample-taker member introduced into the guide means.

These cleaner means comprise, in particular, a rinsing chamber formed in line with the guide means, the rinsing chamber communicating with at least one means for introducing a rinsing liquid and with at least one means for discharging said rinsing chamber and removing the rinsing liquid.

During vertical movements of said sample-taker member in the guide duct of the device of the invention, these cleaner means serve in particular to eliminate a maximum amount of potential dirt from said sample-taker member, regardless of whether the dirt is particles of a stopper, or dried blood on the stopper when the fluid for analysis is blood.

Furthermore, in a particular embodiment of the device of the invention, the cleaner means also comprise at least one wiper gasket disposed in line with the guide means so as to wipe the outside surface of a said sample-taker member introduced into the guide means of the device during the movements in translation of said sample-taker member in the guide means.

Systems for providing sealing between said preparation chambers and the sample-taker member are included in the device for the purpose of physically separating each of the preparation chambers. In a particular embodiment of the invention, the sealing systems may be O-rings.

Another aspect of the present invention relates to a system for sampling, preparing, and fractioned dispensing of samples of a fluid, in particular blood, the system including a preparation and fractioned dispensing device as described above.

In accordance with the present invention, such a system comprises in particular:
  a sample-taker member, in particular a needle, having an end suitable for piercing a stopper of a tube containing a fluid, in particular blood, and at least one orifice suitable for enabling air to be delivered to said tube and for sucking up a sample of fluid in the tube, said orifice being situated laterally in said sample-taker member, and being set back from said end;
  at least one means for sucking up and delivering the sample of fluid, said means being connected to the sample-taker member;
  at least one preparation and dispensing device of the invention as described above, said sample-taker member being inserted in the guide means thereof, said sample-taker member being movable in translation in the guide means along the axis YY' thereof;
  at least one means for dispensing selected volumes of at least one reagent fluid, said means being connected to the introduction orifice of at least one preparation chamber of the preparation and dispensing device; and
  at least one means for receiving and/or analyzing a mixture of an aliquot of the sample of fluid and a determined volume of reagent, said means being connected to the dispensing orifice of the preparation chamber of the preparation and dispensing device.

The system of the invention for sampling, preparing, and fractioned dispensing of fluid samples is thus a system of the "all-in-one" type.

The system is thus optionally capable of piercing the stopper of a tube from which samples are taken, possibly for establishing air flow to bring it to atmospheric pressure, for taking aliquots from a sample of fluid, and for preparing them with one or more appropriate reagents, for dispensing the aliquots as prepared in this way in recovery and/or analysis vessels, and for cleaning the device as a whole.

The reagents are mixed directly in the preparation and dispensing device in the preparation chamber(s).

In addition, the cleaning means of the preparation device serve to eliminate a maximum amount of potential dirt, regardless of whether it comprises dried blood on the stopper or particles of stopper at the end of the sample-taker member.

All of these advantages enable costs to be reduced, provide versatility in use, since it is possible to stack a plurality of preparation chambers, and finally make integration more flexible since it is not essential for the needle to come close to the vessels in order to dispense the aliquots of blood.

In addition, the volume of the aliquots may be modified as a function of analysis requirements.

In a final advantage, even if the point of the sample-taker member is dirtied by waste, it never comes into contact with the preparation chamber, since the orifice for dispensing fluid aliquots is situated laterally on the sample-taker member, thereby avoiding any contamination.

In various preferred configurations, the system of the invention may further include the following advantageous characteristics:
  means for dispensing at least one rinsing fluid for rinsing the sample-taker member, said means being connected to said means for introducing a rinsing fluid into the rinsing chamber of the preparation and dispensing device, and means for sucking up and recovering a said rinsing fluid, said means being connected to means for discharging and removing rinsing fluid from the rinsing chamber of said preparation and dispensing device.

The above-described system of the invention for sampling, preparing, and fractioned dispensing of fluid samples facilitates operations of fractioned dispensing of samples of fluid, in particular blood, for analysis in automatic analysis machines.

The system makes it possible in particular to perform fractioned dispensing of blood samples using the following steps:
  a) sucking up a sample of a fluid contained in a tube into the sample-taker member of the system, the sample-taker member previously being guided to move in translation along the axis YY' through the device until the end of the sample-taker member is introduced into the tube containing the fluid; then
  b) moving, typically upward, said sample-taker member in translation along the axis YY' of the guide means of the preparation and dispensing device until the orifice of the sample-taker member is brought into at least one preparation chamber of the preparation and dispensing device; and finally
  c) simultaneously or otherwise dispensing an aliquot of the taken fluid sample via the orifice of the sample-taker member and a determined volume of a reagent fluid into the preparation chamber of the preparation and dispensing device, said aliquot and said determined volume of reagent fluid being mixed and then discharged together under the pressure of the reagent fluid to means for recovering and/or analyzing said mixture via the dispensing orifice of the preparation and dispensing device.

The preparation and fractioned dispensing method of the invention also provides that after the fluid sample has been taken from the tube and before a said aliquot has been dispensed into said preparation chamber of the preparation and dispensing device, the sample-taker member that has been in contact with the fluid is cleaned by using the cleaner means of the preparation and dispensing device. This eliminates or at least minimizes the risk of the sample-taker member being dirtied and thus of the analyses being disturbed.

Finally, when the tubes from which the fluid samples are to be taken are at reduced pressure, the method of the invention provides that prior to taking a said fluid sample from a said tube that is closed by a stopper, the pressure inside said tube is brought into equilibrium, where necessary, by means of said sample-taker member.

BRIEF DESCRIPTION OF THE DRAWINGS

Other characteristics and advantages of the present invention appear better on reading the following description made by way of non-limiting illustration and with reference to the accompanying drawings, in which.

MORE DETAILED DESCRIPTION

The device, the system including said device, and the method using system are intended more particularly for hematological analysis, however they are equally suitable for use in any kind of fluid analysis. Nevertheless, the description below focuses only on the application in the field of hematological analysis of blood samples.

Figure 1A:
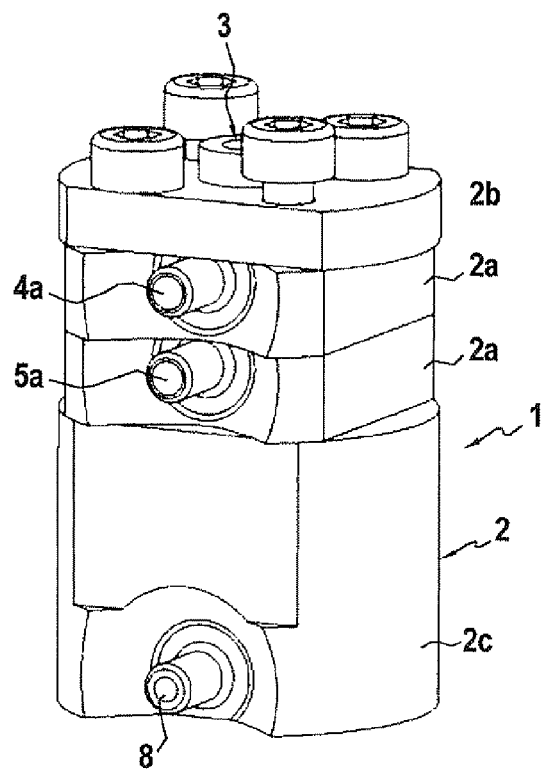
FIG. 1A is a perspective view of a preparation and fractioned dispensing device in a preferred embodiment in accordance with the invention.
Figure 1B:
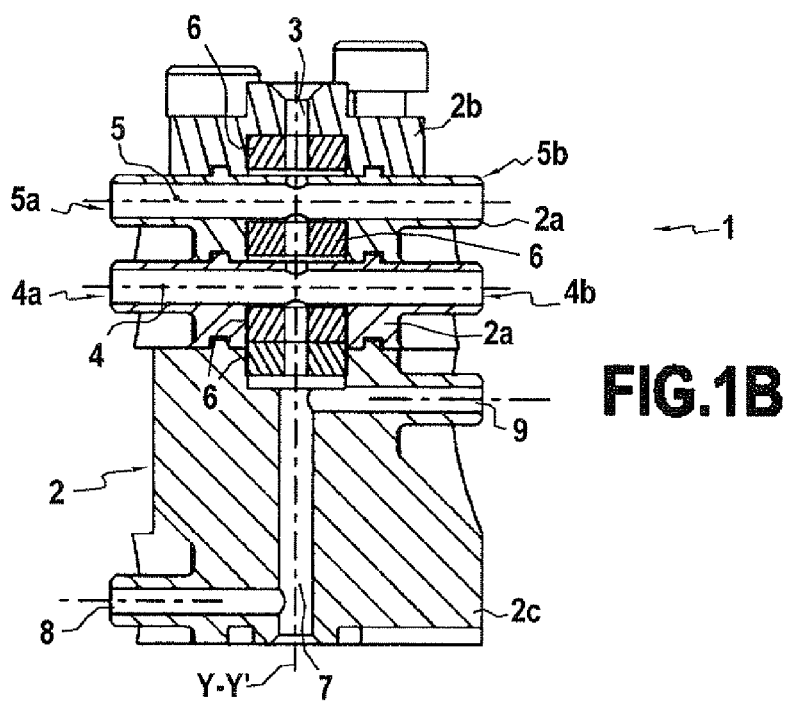
FIG. 1B is a section view on a longitudinal midplane of the preparation and dispensing device shown in FIG. 1A.

With reference initially to FIGS. 1A and 1B, there is shown, in a first aspect of the invention, a device 1 for preparing and fractioned dispensing of samples making it possible in automatic manner to divide samples into a plurality of aliquots and prepare and dispense them for measuring different parameters.

The device 1 essentially comprises a body 2 pierced on its axis YY' by a cylindrical duct 3 that opens out in the top and bottom surfaces of the body 2 of the device.

The open-ended duct 3 constitutes guide means adapted to receive a member for taking a sample and to guide it in translation along the axis YY' of the device 1, where such a member may be a needle 10 as shown and described below with reference to FIG. 2 et seq.

In addition to the duct 3, the body 2 of the device 1 also has preparation chambers 4 and 5 that are superposed one on the other, each of them being formed by a duct passing through the body 2 on a respective axis, which axes are preferably parallel to each other and intersect the axis YY' of the device 1.

Both preparation chambers 4 and 5 intersect the vertical guide duct 3 pierced vertically through the body 2 of the device 1 and thus, in the absence of the sample-taker member, they communicate therewith.

Furthermore, each preparation chamber 4 and 5 has at its ends a first open orifice and a second open orifice forming respectively introduction orifices 4a and 5a for introducing at least one analysis reagent, and dispensing orifices 4b, 5b for dispensing a mixture formed of a said reagent and an aliquot of blood prepared in each of the preparation chambers 4, 5.

In order to ensure good sealing between each of the preparation chambers 4 and 5 and the guide duct 3 when a sample-taker member such as a needle is inserted into said guide duct, the device 1 includes sealing gaskets 6 in its body 2, which gaskets are disposed on either side of openings for interconnecting the guide duct 3 and each of the preparation chambers 4 and 5. It should also be observed that it is useful for the sealing gaskets, at least those that are situated at the bottom(s) of the preparation chamber(s), to present elasticity such that in the absence of the sample-taker member, the central orifice of the gasket closes. This avoids any downward loss of fluid when the sample-taker needle is no longer engaged in the gasket and avoids any possible contamination. In the absence of such gaskets, it is necessary for the device-manipulating sequences to be such that the needle blocks the orifice of the gasket of the preparation chamber in question during mixing manipulations within the preparation chamber.

The body 2 of the device 1 also includes a rinsing chamber 7 formed to extend the guide duct 3, on the axis YY' of the device, which rinsing chamber constitutes a duct that opens into the guide duct 3 and communicates therewith via its top end.

At its bottom end, the rinsing chamber 7 communicates with a feed duct 8 formed through the base of the body 2 of the device 1 and at its top ends it communicates with a discharge duct 9 likewise formed in the body 2 of the device.

These ducts 8 and 9 serve respectively to introduce a rinsing liquid into the chamber and to extract it therefrom for the purpose of cleaning the end of a sample-taker member inserted in the guide duct 3 of the device as it moves in translation along the axis YY' of the device 1 while said device is in operation, as described below.

In addition, the device 1 also has a gasket and, where appropriate, a wiper gasket at the open end of the chamber 7 for the purpose of removing any dirt that might be deposited on the sample-taker member as it enters into the chamber 7. This wiper gasket may be of the same nature as the sealing gasket used for physically separating the preparation chambers, however it could equally well be of some other nature.

The body 2 of the preparation and fractioned dispensing device of the invention is advantageously made of a biologically inert material. The material may be polypropylene, polymethyl methacrylate (PMMA), polyethylene, glass, stainless steel, Teflon®, or PEEK®, or any other material well known to the person skilled in the art.

Furthermore, although it is possible for the body 2 of the device 1 of the invention to be made as a single piece, e.g. by molding, it is preferable, as shown in the embodiment of FIGS. 1A and 1B, to make the body 2 in modular form built up from distinct modules that are suitable for being assembled with one another, such as in particular modules 2a for making one or more preparation chambers and a module 2b for covering the module(s) 2a to provide a preparation chamber, and also a module 2c having formed therein the rinsing chamber 7 with its feed and discharge ducts 8 and 9, the modules 2b and 2c being suitable respectively for being engaged under a module 2a by any suitable engagement or connection means, in particular tenon and mortise means or tongue and groove means formed in the engaging surfaces of each the modules 2a, 2b, and 2c, with the assembly being held together securely by an assembly screw.

A modular construction of the body 2 of the preparation and fractioned dispensing device of the invention presents the particular advantage of enabling the device 1 to have functional modularity depending on the type of automatic analyzer in which it is to be used.

In particular, a modular structure makes it possible to adapt the number of preparation chambers of the device 1 by multiplying the number of modules 2a and stacking them on one another, each module defining one said chamber.

In addition, the modular structure of the body also presents the advantage of making the device 1 easier to maintain by making it suitable for being disassembled, thus making it possible firstly to clean each of the modules 2a, 2b, and 2c on a regular basis, and also making it easy to change each of the sealing gaskets 6 of the device since, in a body of modular structure, the gaskets are received in cylindrical counterbores on the axis of the guide ducts 3 formed on the longitudinal axis YY' of the device.

Thus, when a sealing gasket fails, it suffices to separate the modules 2a, 2b, and 2c of the device in order to remove the failed gasket 6 and replace it by a new gasket, and then to reassemble the assembly.

If the body 2 of the device 1 is made as a single piece, the sealing system could then be provided and implemented by all or part of the single piece 2, in particular by making it out of a material that is suitable for making the sealing system.

The device 1 of the invention for preparing and fractioned dispensing of blood samples makes it possible in simple, safe, and fast manner to take a sample of blood from a tube, whether open or closed by a stopper, and to subdivided it into a plurality of aliquots of very small volume, to prepare these various aliquots inside the preparation chambers 4 and 5 with selected volumes of different reagents, and to dispense the mixtures to recovery and/or analysis means.

Figure 2:
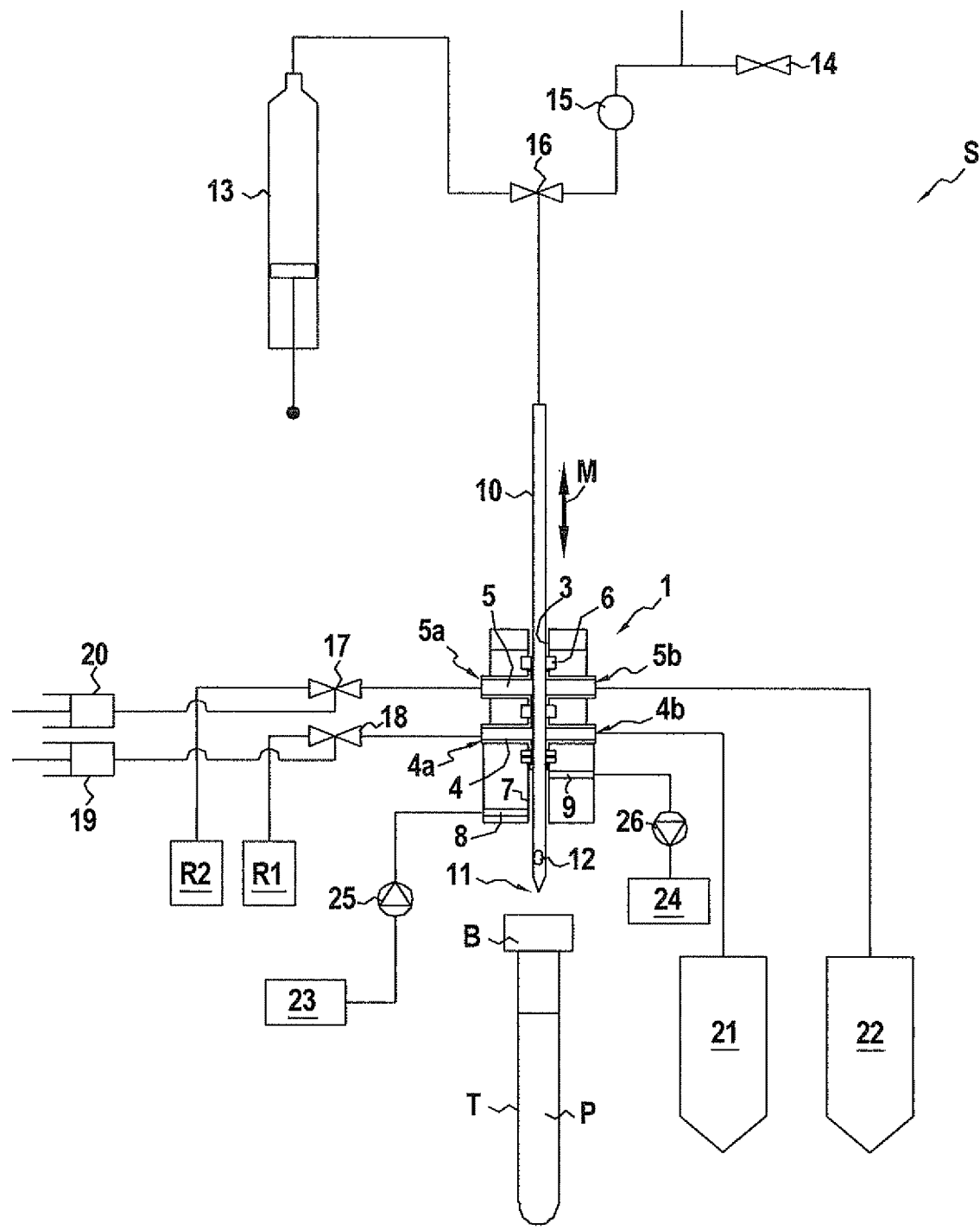
FIG. 2 shows a system for sampling, preparing, and fractioned dispensing of blood samples in accordance with the present invention, the system incorporating a preparation and fractioned dispensing device as shown in FIGS. 1A and 1B.

The device 1 of FIGS. 1A and 18 was designed by the Applicant in particular to form an integral portion of a complete system S for taking, preparing, and dispensing fractioned fluid samples, in particular blood samples, that are to be analyzed, as shown in FIG. 2.

This system S for taking, preparing, and fractioned dispensing comprises firstly a device 1 for preparing and fractioned dispensing, as described above and shown in FIGS. 1A and 1B having a sample-taker member 10 inserted in the guide duct 3 thereof, which member is preferably in the form of an elongate needle inserted along the axis YY' in the duct 3 of the device 1 and movable in translation along the axis YY' in said duct 3 by means of a mover device.

The sample-taker member 10 has a pointed first end 11 with a sample-taking and dispensing orifice 12 formed close thereto, being set back a little from the pointed end and thus located on one side of the sample-taker member.

The sample-taker needle 10 may have a single lateral orifice 12, however it could also have a plurality of holes so as to constitute a first filter for preventing the passage of pieces from the stoppers that might arise due to the stoppers B of the tubes T being pierced.

The size and the configuration of these holes may vary and it is possible to envisage having a plurality of configurations. Nevertheless, the area(s) of the hole(s) 12 must never be greater than the section of the preparation chambers.

The sample-taker member may also have multiple channels, with some of them being used for taking samples and others for delivering air to a tube, where necessary. Similarly, the sample-taker member may be made up of a plurality of sample-taker needles.

At its end opposite from its pointed tip, the sample-taker member 10 is connected by suitable means to a device 13 for sucking in and blowing out blood, such as a motor-driven syringe, for example.

Furthermore, the system S shown in FIG. 2 also has means for feeding air to a tube T containing blood. These means comprise an air-connection valve 14 connected in series to a pressure sensor 15, itself connected to the sample-taker member 10 via a valve 16.

Advantageously, and where necessary, these air-feeder means serve to ensure that a tube T closed by a stopper B is at atmospheric pressure before a sample is taken, since any high or low pressure inside the tube T can disturb the sucking in of a sample by the needle 10 in the tube T.

Between the syringe 13, the air supply elements 14, 15 and the sample-taker needle 10, there is placed a valve 16 for performing hydraulic switching enabling communication to be established in alternation and in application of a determined cycle between the sample-taker needle 10 and the syringe 13 or between the sample-taker needle 10 and the system constituted by the elements 14 and 15 for supplying air to the tube.

As shown in this figure, the tube T containing a fluid P for analysis is placed under the preparation and dispensing device 1, or at least on the side of the device 1 opposite from the side of the device 1 into which the sample-taker member 10 is made to penetrate. Here, the tube T is placed beside the bottom surface of the device 1, which is advantageous from a practical point of view for controlling bringing the tube to face the bottom orifice of the guide means of the device 1. Otherwise, it remains possible, although more difficult, for the tube to be turned upside-down with the sample-taker member then rising through the device of the invention so as to take the sample and then being lowered so as to dispense it into the preparation chambers.

The preparation chambers 4, 5 of the device 1 are hydraulically connected via their respective reagent introduction orifices 4a and 5a to respective reagent tanks R1 and R2. Between said tanks R1 and R2 and the orifices 4a and 5a of the preparation chambers, there are arranged valves 17, 18 that enable determined volumes of reagent to be taken from each of the tanks R1, R2, e.g. with the help of motor-driven syringes 19 and 20, and introduced into the preparation chambers 4 and 5 so as to mix the reagents with respective aliquots dispensed by the sample-taker needle into said chambers 4 and 5, as described below.

The mixing between the blood aliquots and the reagents takes place directly at the outlet from the needle 10 in the flow of reagent within the preparation chambers 4, 5. The device 1 thus makes better mixing possible between the sample and the reagent.

Via their dispensing orifices 4b, 5b, the preparation chambers 4, 5 of the device 1 are hydraulically connected to respective recovery vessels and/or analysis means 21, 22 into which the mixtures formed in the chambers 4, 5 are dispensed as described in greater detail below, each mixture being between a reagent and an aliquot of blood previously deposited by the sample-taker member in said chamber.

Thus, without it being necessary to move the device, the aliquots mixed with the reagents are dispensed into the various recovery vessels and/or analysis means 21, 22. The sample-taker needle 10 does not need to be moved over those vessels, all that is required is respective pipes for conveying the blood mixed with the reagent to the vessels 21, 22 from the dispensing orifices 4b, 5b of the dilution chambers 4, 5 of the device 1.

The system S also has a tank of rinsing liquid 23 connected to the rinsing channel 8 of the device 1 via pipes and a dispensing pump 25, together with a recovery tank 24 connected to the rinsing liquid suction channel of the device 1 via a pipe and a suction pump 26.

These rinsing means thus make it possible to introduce a rinsing liquid from the tank 23 into the rinsing chamber 7 of the device 1 for the purpose of cleaning the sample-taker member 10 as it rises towards the preparation chambers 4, 5 of the device 1, and simultaneously to suck out the introduced rinsed liquid, possibly mixed with pieces of the tube stopper, via the channel 7 to the recovery tank 24.

In well-known manner for the person skilled in the art, the system S and the set of elements making it up, in particular the moving elements thereof, may be (and in practice are) driven and controlled by an automatic control unit that is not shown in the figures. This control unit may include in particular a desk and computer control means enabling the operation of the system S and of each of its components to be programmed, and more generally serving to control the operation of the automatic analyzer assembly in which the system S is installed and used.

The operation of the device 1 of the present invention for preparing and fractioned dispensing, and the operation of the system S for taking, preparing, and fractioned dispensing and incorporating said device is described in greater detail below with reference to FIGS. 3A to 3C.

Figure 3A:
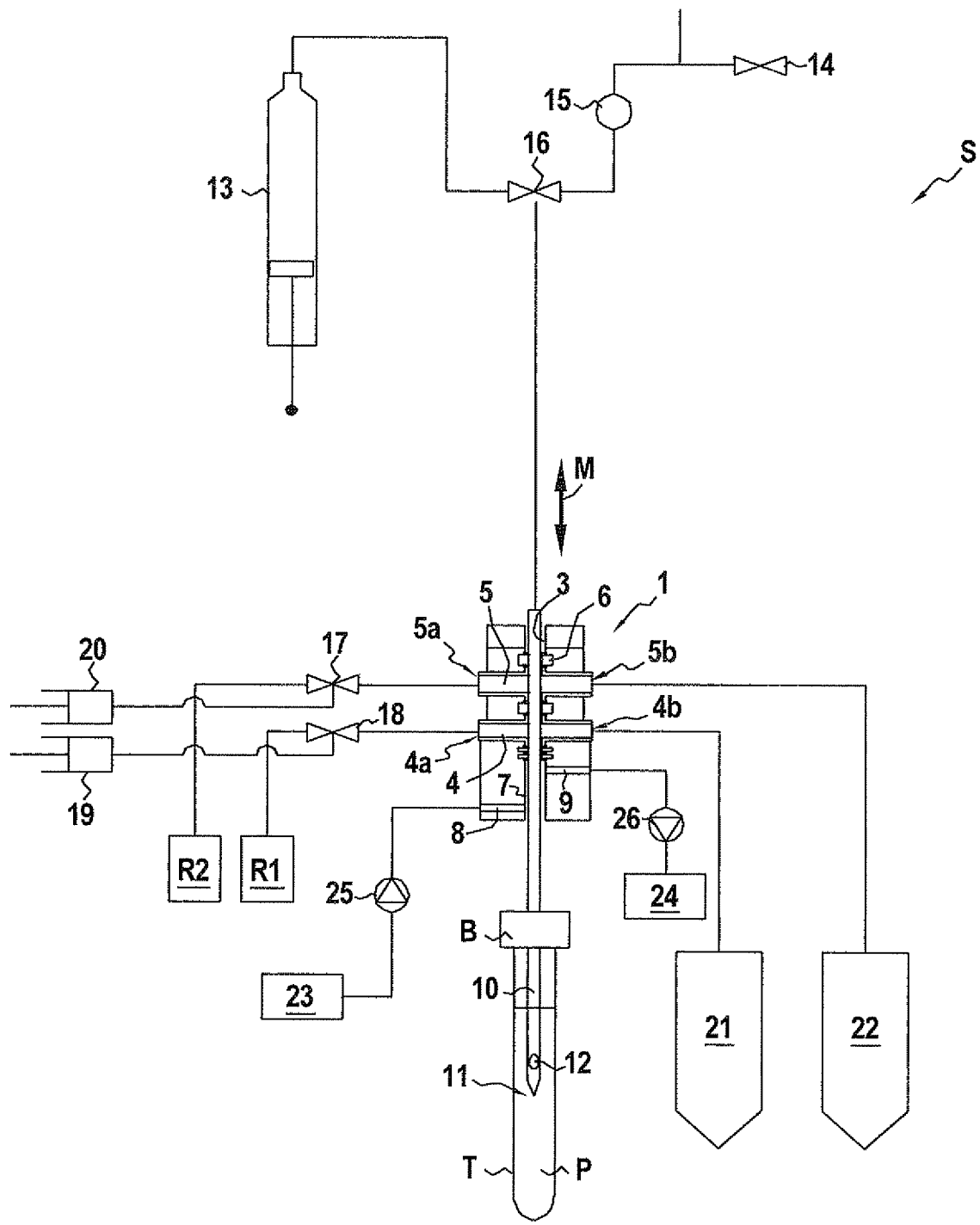
FIGS. 3A to 3C show how sampling, preparing, and fractioned dispensing of blood samples take place in the system as shown in FIG. 2 according to the method of the present invention.

With reference initially to FIG. 3A, a sample of blood is firstly taken by means of the sample-taker needle 10 from a tube T that is closed by a stopper B and that contains a blood specimen P. It should be observed that the system S is also capable of operating with tubes T that are not closed by stoppers B.

For this purpose, the needle 10 is moved in translation along the axis YY' of the device 1 along the guide duct 3 of the device 1 until the pointed end 11 passes through the stopper B of the tube T. The pressure inside the tube T is then measured using the pressure sensor 15. The valve 16 establishes communication between the orifice 12 of the needle 10 and the pressure sensor 15. The pressure sensor acts via the orifice 12 to determine the pressure that exists inside the tube. If the tube T is at a reduced pressure (as happens with a tube that has not been opened and then reclosed, which is the usual situation), the balancing valve 14 is opened to rebalance the pressure inside the tube T of blood.

Once atmospheric pressure is reached, the valve 16 closes hydraulic communication between the needle 10 and the air feed means 14, 15, and it establishes a connection between the needle 10 and the syringe 13.

The needle 10 is then lowered until it is immersed sufficiently in the tube T to enable the sample to be taken via the orifice(s) 12 in the needle 10.

Thereafter, the piston of the syringe 13 is actuated so as to take a volume V of sample of blood for analysis.

Once this sample has been taken, the needle 10 is raised in the device 1. The end 11 of said needle then penetrates into the rinsing chamber 7 of the device 1 in which it is cleaned.

The pump 25 is then actuated to introduce a stream of rinsing liquid into the rinsing chamber 7 via the channel 8 and from the tank 23. Simultaneously, the pump 26 is also actuated so as to suck out air and rinsing liquid from the chamber 7 via the channel 9, thereby establishing turbulence along the sample-taker needle 10 and thus enabling it to be thoroughly cleaned, the air and the rinsing liquid sucked out by the pump 26 being collected in the tank 24.

If any residual dirt remains on the needle, the gaskets 6 disposed ahead of the first preparation chamber 4 enable any residual trace of dirt to be wiped off the sample-taker needle. It should be observed that the gaskets 6 may be identical to or different from the gaskets disposed between each of the preparation chambers.

Figure 3B:
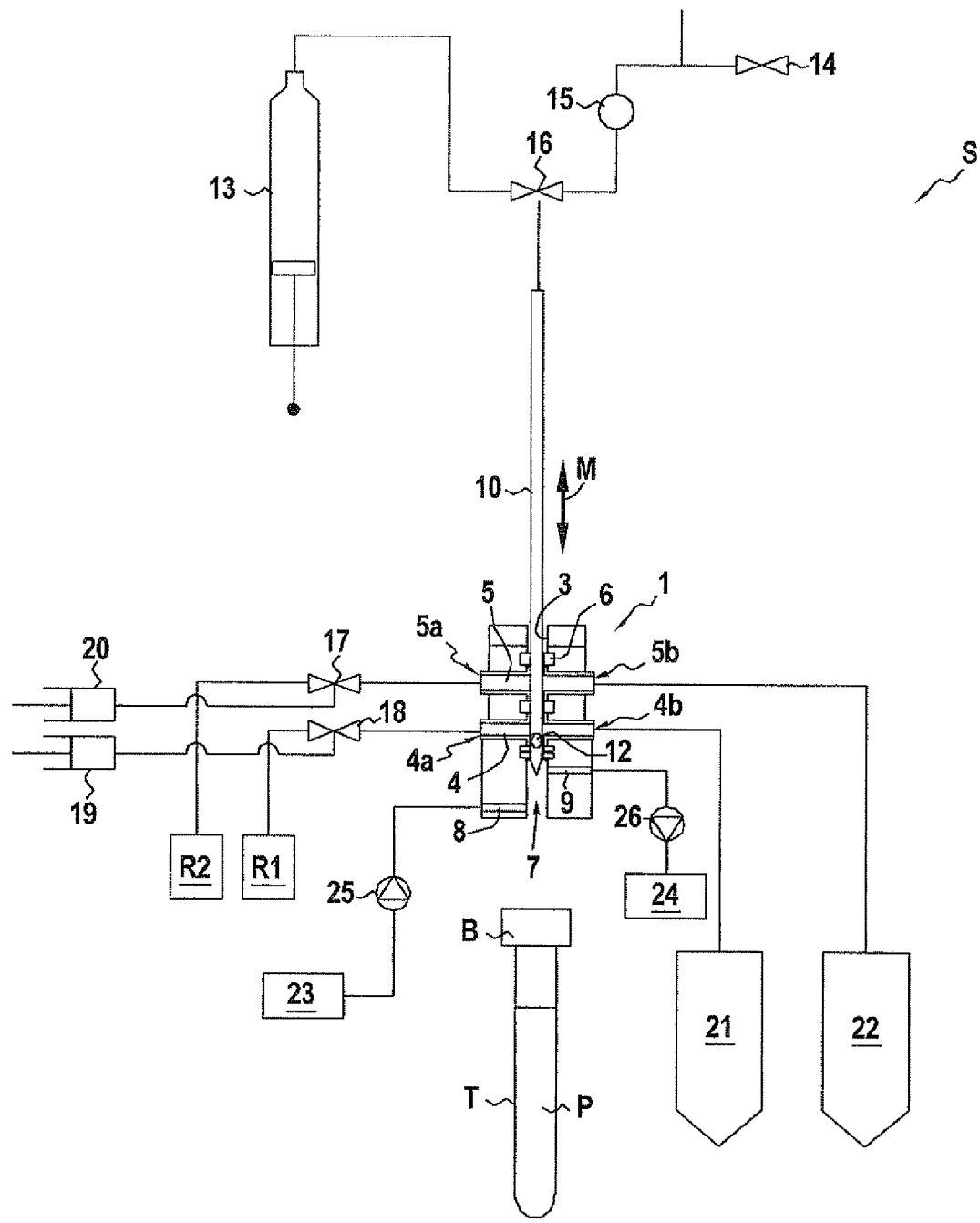

Once the sample-taker needle 10 has been cleaned, it is then once more raised in translation along the duct 3 of the device 1 until the orifice 12 of said needle is positioned in the first preparation chamber 4 of the device 1, as shown in FIG. 3B.

The syringe 13 then pushes a first aliquot of blood a1 of a determined volume into the preparation chamber 4.

Simultaneously with the aliquot a1 being deposited in the chamber 4, the valve 18 that is connected to the reagent tank R1 and to the introduction orifice 4a of the preparation chamber 4 is opened in order to introduce a determined volume of reagent R1 that is sucked up and then pushed into the chamber 4 by the syringe 19 so as to mix the aliquot a1 with the reagent.

Mixing is performed at the pressure with which the reagent is introduced into the preparation chamber 4 from the tank R1, and at the same pressure the mixture is then dispensed via the dispensing orifice 4b of the preparation chamber 4 to a recovery and/or analysis vessel 21.

Figure 3C:
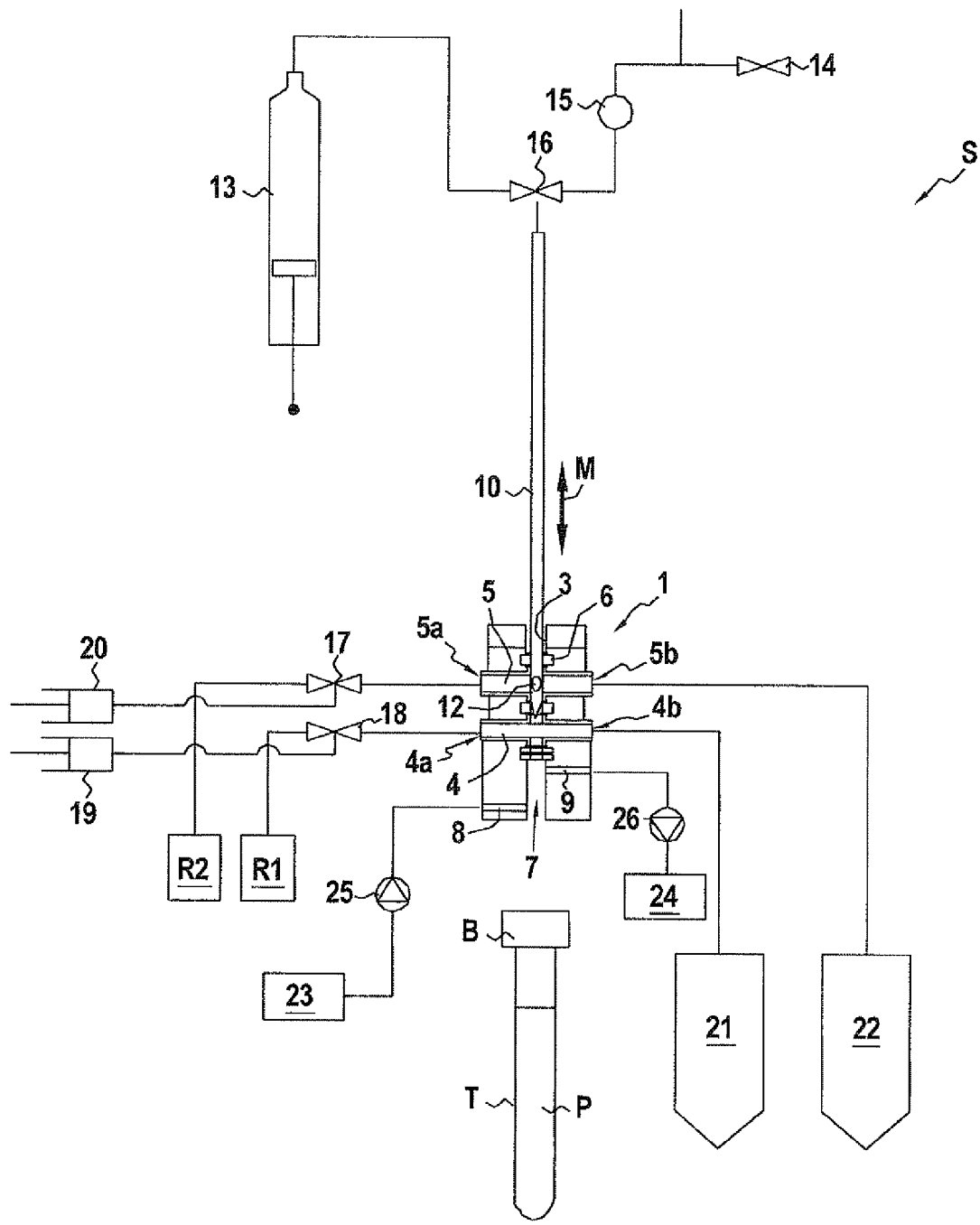

Once the first aliquot a1 has been dispensed in full, the sample-taker needle 10 is raised along the duct 3 of the device 1 until the orifice 12 of said needle is positioned in the second preparation chamber 5, as shown in FIG. 3C.

A second aliquot a2 of blood is then dispensed into the preparation chamber 5. The piston of the syringe 13 then pushes a determined volume of blood to form the aliquot a2 into the chamber 5 and simultaneously the dispensing valve 19 is opened to introduce a predetermined volume of reagent into the chamber 5 via the orifice 5a, which volume is taken from the tank R2, the reagent being sucked up and pushed out by a motor-driven syringe 20.

The aliquot a2 is then mixed with the reagent in the chamber 5 and is dispensed via the dispensing orifice 5b to a second recovery and/or analysis vessel 22.

Thereafter the sample-taker needle 10 is lowered back down the duct 3 into the cleaning chamber 7 where it is emptied and then cleaned and dried prior to starting a new cycle of taking and/or dispensing a new sample of blood.

The device 1 of the invention for preparing and fractioned dispensing, and the system S incorporating the device thus enable a sample of fluid to be dispensed after being fractioned into multiple aliquots without moving the needle between the tube containing the fluid for analysis and the reception and/or analysis vessel, merely by aligning the orifice of the needle 10 with the preparation and dispensing chambers of the device 1 of the invention for preparing and fractioned dispensing.

Finally, it should be observed that various implementations may be provided on the principles of the invention. In particular, the axis YY' is not necessarily vertical, and fractioning may be implemented on the principle of the invention with the sample-taker member moving in translation along some direction other than the vertical direction, as used in the description. The invention relates to any system in which a tube or a receptacle, where appropriate one that is adapted to receive a lateral perforation, is in alignment with means for guiding a preparation and dispensing device of the invention in order to take a sample with the help of a sample-taker member that passes through the device, with it being possible for the axis of the alignment to be vertical, horizontal, or at an arbitrary angle. The characteristics of the invention in which the preparation chambers are not necessarily leaktight, make such configurations possible.

What is claimed is:

1. A device for the preparation and fractioned dispensing of samples of a fluid contained in a tube, wherein the device comprises a body comprising:
   guide means adapted to receive a sample-taker member for taking samples of a fluid and for guiding it in translation within the device along an axis YY', the guide means being constituted by a channel passing through the device along the axis YY' and opening out in opposite sides of said device, the channel being shaped to receive the sample-taker member and to guide it in translation along the axis YY' through the device until the end of the sample-taker member is introduced into the tube containing the fluid; and
   at least one preparation chamber including an introduction orifice and at least one dispensing orifice, wherein the guide means passes through the preparation chamber and communicates therewith such that an aliquot of a sample of fluid is dispensed into the chamber by the sample-taker member in a determined position thereof within the guide means, is mixed with an appropriate reagent introduced by means of the introduction orifice, and the mixture is expelled from the chamber by means of the dispensing orifice.

2. A device according to claim 1, wherein the preparation chamber is constituted by a channel passing through the device, thereby forming two orifices, respectively the introduction orifice and the dispensing orifice of the preparation chamber.

3. A device according to claim 2, wherein the chamber of the preparation chamber comprises the channel oriented along an axis that is perpendicular to the axis YY' of the guide means.

4. A device according to claim 1, including cleaner means for cleaning the sample-taker member introduced into the guide means.

5. A device according to claim 4, wherein the cleaner means comprises a rinsing chamber formed in line with the guide means, the rinsing chamber communicating with at least one means for introducing a rinsing liquid and with at least one means for discharging said rinsing chamber and removing the rinsing liquid.

6. A device according to claim 4, wherein the cleaner means includes at least one wiper gasket disposed in line with the guide means so as to wipe the outside surface of a said sample-taker member introduced into the guide means of the device during the movements in translation of said sample-taker member in the guide means and/or the rinsing chamber.

7. A device according to claim 1, presenting a modular structure, each module supporting at least one preparation chamber and a portion of the guide means, and each module being suitable for being stacked with other modules in the direction of the axis YY'.

8. The device according to claim 1, wherein the fluid is blood.

9. A system for the preparation and fractioned dispensing of samples of a fluid comprising:
a tube comprising a fluid;
a sample-taker member configured to be introduced into the tube;
means for introducing the fluid into the sample-taker member from the tube;
at least one supply of an appropriate reagent;
at least one means for receiving and/or analyzing a mixture of an aliquot of the sample of fluid and a determined volume of reagent; and
a device comprising:
guide means adapted to receive the sample-taker member for taking samples of the fluid and for guiding it in translation within the device along an axis YY', the guide means being constituted by a channel passing through the device along the axis YY' and opening out in opposite sides of the device, the channel being shaped to receive the sample-taker member and to guide it in translation along the axis YY' through the device until the end of the sample-taker member is introduced into the tube containing the fluid; and
at least one preparation chamber including an introduction orifice and at least one dispensing orifice, wherein the guide means passes through the preparation chamber and communicates therewith such that an aliquot of a sample of fluid is dispensed into the chamber by the sample-taker member in a determined position thereof within the guide means, is mixed with an appropriate reagent introduced by means of the introduction orifice, and the mixture is expelled from the chamber by means of the dispensing orifice.

10. A system according to claim 9, wherein the device further comprises a rinsing chamber formed in line with the guide means, and the system further comprises:
means for dispensing at least one rinsing fluid for rinsing the sample-taker member,
means for introducing the rinsing fluid into the rinsing chamber of the device, the introducing means being coupled to the dispensing means, and
means for discharging the rinsing chamber and removing the rinsing fluid from the rinsing chamber.

11. A system according to claim 9, further including air flow means communicating with the sample-taker member.

12. The system according to claim 9, wherein the fluid is blood.

13. The system according to claim 9 wherein the sample taker member is a needle.

14. A method for the preparation and fractioned dispensing of a sample of a fluid comprising the steps of:
providing a device comprising:
guide means adapted to receive the sample-taker member for taking samples of the fluid and for guiding it in translation within the device along an axis YY', the guide means being constituted by a channel passing through the device along the axis YY' and opening out in opposite sides of the device, the channel being shaped to receive the sample-taker member and to guide it in translation along the axis YY' through the device until the end of the sample-taker member is introduced into the tube containing the fluid; and
at least one preparation chamber including an introduction orifice and at least one dispensing orifice, wherein the guide means passes through the preparation chamber and communicates therewith such that an aliquot of a sample of fluid is dispensed into the chamber by the sample-taker member in a determined position thereof within the guide means, is mixed with an appropriate reagent introduced by means of the introduction orifice, and the mixture is expelled from the chamber by means of the dispensing orifice,
inserting a sample-taker member into one end of the guide means of the device,
guiding the sample-taker member in translation through the body of the device, such that the sample-taker member exits the guide means on the opposite side of the device;
introducing the sample taker member into a tube comprising a fluid,
introducing the fluid into the sample-taker member from the tube;
guiding the sample-taker member in translation through the device such that at a determined position of the sample-taker member, an aliquot of a sample of the fluid is dispensed into the preparation chamber,
introducing an appropriate reagent into the preparation chamber by means of the introduction orifice such that the aliquot mixes with the reagent, and
expelling the mixture from the chamber by means of the dispensing orifice.

15. A method according to claim 14, further comprising the steps of:
providing a rinsing chamber in the device, the rinsing chamber formed in line with the guide means, and
after introducing the fluid sample into the sample-taken member from the tube and before dispensing an aliquot into the preparation chamber of the device, cleaning at least a portion of the sample-taker member within the rinsing chamber.

16. A method according to claim 14, further comprising the step of balancing the pressure inside the tube by means of the sample-taker member before introducing the fluid sample into the sample-member from the tube.

17. The method according to claim 14, wherein the fluid is blood.

* * * * *